US010618863B2

(12) United States Patent
Jouanneau et al.

(10) Patent No.: US 10,618,863 B2
(45) Date of Patent: *Apr. 14, 2020

(54) METHOD FOR MANUFACTURING 1,4-BIS (4-PHENOXYBENZOYLBENZENE) AT AN ELEVATED TEMPERATURE

(71) Applicant: ARKEMA FRANCE, Colombes (FR)

(72) Inventors: Julien Jouanneau, Corneville sur Risle (FR); Guillaume Le, Herouville Saint Clair (FR); Jérome Amstutz, Charly (FR)

(73) Assignee: ARKEMA FRANCE, Colombes (FR)

( * ) Notice: Subject to any disclaimer, the term of this patent is extended or adjusted under 35 U.S.C. 154(b) by 12 days.

This patent is subject to a terminal disclaimer.

(21) Appl. No.: 15/981,284

(22) Filed: May 16, 2018

(65) Prior Publication Data
US 2018/0334418 A1  Nov. 22, 2018

(30) Foreign Application Priority Data
May 16, 2017 (EP) .................... 17305559

(51) Int. Cl.
C07C 45/80 (2006.01)
C07C 45/46 (2006.01)
C08G 65/40 (2006.01)
C08G 61/12 (2006.01)

(52) U.S. Cl.
CPC .............. C07C 45/46 (2013.01); C07C 45/80 (2013.01); C08G 61/127 (2013.01); C08G 65/4012 (2013.01); C08G 65/4093 (2013.01); C08G 2261/3442 (2013.01); C08G 2261/45 (2013.01); C08G 2650/62 (2013.01)

(58) Field of Classification Search
USPC ........................................................ 528/176
See application file for complete search history.

(56) References Cited

U.S. PATENT DOCUMENTS

| 4,704,448 | A | 11/1987 | Brugel |
| 4,709,007 | A | 11/1987 | Jansons et al. |
| 4,716,211 | A | 12/1987 | Clendinning et al. |
| 4,794,155 | A | 12/1988 | Woo et al. |
| 4,816,556 | A | 3/1989 | Gay et al. |
| 4,826,947 | A | 5/1989 | Jansons et al. |
| 4,827,041 | A | 5/1989 | Ford et al. |
| 4,891,167 | A | 1/1990 | Clendinning et al. |
| 4,918,237 | A | 4/1990 | Corbin et al. |
| 4,931,530 | A | 6/1990 | Fukawa et al. |
| 5,137,988 | A | 8/1992 | Matzner et al. |
| 5,258,491 | A | 11/1993 | Agreda et al. |
| 5,734,005 | A | 3/1998 | Daniels et al. |
| 10,344,125 | B2 | 7/2019 | Le et al. |
| 10,428,002 | B2 | 10/2019 | Jouanneau et al. |
| 2015/0183918 | A1 | 7/2015 | Le et al. |
| 2018/0334419 | A1 | 11/2018 | Jouanneau et al. |
| 2018/0334420 | A1 | 11/2018 | Le et al. |
| 2018/0334538 | A1 | 11/2018 | Le et al. |
| 2019/0040189 | A1 | 2/2019 | Le et al. |
| 2019/0077739 | A1 | 3/2019 | Jouanneau et al. |
| 2019/0135721 | A1 | 5/2019 | Jouanneau et al. |
| 2019/0152886 | A1 | 5/2019 | Jouanneau et al. |

FOREIGN PATENT DOCUMENTS

| EP | 0 192 260 A1 | 8/1986 |
| EP | 0 268 112 A2 | 5/1988 |
| EP | 0 298 771 A2 | 1/1989 |
| EP | 0 316 133 A2 | 5/1989 |
| EP | 0 268 112 A3 | 11/1989 |
| EP | 3 438 085 A1 | 2/2019 |
| GB | 2 287 031 A | 9/1995 |
| IN | 193687 | 7/2004 |
| SU | 445 643 A | 12/1975 |
| WO | WO 95/23821 A1 | 9/1995 |

OTHER PUBLICATIONS

U.S. Appl. No. 15/981,439, Jouanneau et al.
U.S. Appl. No. 15/981,498, Jouanneau et al.
U.S. Appl. No. 15/982,625, Le et al.
U.S. Appl. No. 15/982,453, Jouanneau et al.
U.S. Appl. No. 15/982,549, Le et al.
Database WPI Week 197630, AN 1976-57263X, Dec. 19, 1975, vol. 1976, No. 30,31, 1 page, Thomson Scientific, London, GB (XP002775200).
Banihashemi, Ahmad, et al., "New heat stable polyethers, polyketones and polysulfones", Macromolecular Chemistry and Physics, vol. 200, No. 10, Oct. 1, 1999, pp. 2284-2293, Wiley-VCH Verlag GmbH, Weinheim, DE (XP055420800).
Baysec, Sebnem, et al., "Very High Solid State Photoluminescence Quantum Yields of Poly(tetraphenylethylene) Derivatives", Macromolecular Rapid Communications, vol. 37, No. 22, Sep. 26, 2016, pp. 1802-1806, Wiley-VCH Verlag GmbH & Co. KGaA, Weinheim, DE (XP055420789).
Fukawa, Isaburo, et al., "Preparation of Dibenzofuran-Type Amorphous Polyetherketone by Novel Etherification Reaction", Journal of Polymer Science: Part A: Polymer Chemistry, 1992, pp. 1977-1985, vol. 30 (XP055420842).
March, Jerry, "Advanced Organic Chemistry", Dec. 31, 1985, p. 333, copyright page, John Wiley & Sons, New York (XP002775202).
Mithyantha, et al. , "A process for the purification of 1,4-bis(4-phenoxybenzoyl)benzene", Database CAPLUS [Online], Aug. 23, 2006, 1 page, Chemical Abstracts Service, Columbus, OH (XP002775201).

(Continued)

Primary Examiner — Terressa Boykin
(74) Attorney, Agent, or Firm — Buchanan Ingersoll & Rooney P.C.

(57) ABSTRACT

A method for manufacturing 1,4-bis 4-phenoxybenzoyl) benzene, including: providing a reactant mixture including terephthaloyl chloride and diphenyl ether in a solvent; adding a Lewis acid to the reactant mixture, so as to obtain a product mixture; wherein the temperature of the reactant mixture is greater than 5° C. during at least part of the step of adding the Lewis acid to the reactant mixture.

17 Claims, No Drawings

(56) References Cited

OTHER PUBLICATIONS

Streitwieser, Andrew, et al., "Introduction to Organic Chemistry", Dec. 31, 1981, p. 544, copyright page, MacMillan Publishing Co., Inc., New York (XP002775203).
European Search Report in application No. EP 17305559.1, dated Nov. 9, 2017, European Patent Office, Munich, DE, 10 pages.
European Search Report in application No. EP 17305561.7, dated Nov. 3, 2017, European Patent Office, Munich, DE, 5 pages.
European Search Report in application No. EP 17305562.5, dated Dec. 6, 2017, European Patent Office, Munich, DE, 10 pages.
European Search Report in application No. EP 17305581.5, dated Nov. 24, 2017, European Patent Office, Munich, DE, 6 pages.
European Search Report in application No. EP 17305582.3, dated Nov. 8, 2017, European Patent Office, Munich, DE, 7 pages.
European Search Report in application No. EP 17305583.1, dated Aug. 22, 2017, European Patent Office, Munich, DE, 8 pages.
Jouanneau, Julien M., et al., U.S. Appl. No. 15/981,439 entitled "Method for Manufacturing 1,4-Bis(4-Phenoxybenzoyl)Benzene in Supersaturation Conditions," filed in the U.S. Patent and Trademark Office May 16, 2018.
Jouanneau, Julien, et al., U.S. Appl. No. 15/981,498 entitled "Method for Manufacturing 1,4-Bis(4-Phenoxybenzoyl)Benzene Using Substantially Non-Hydrolyzed Terephthaloyl Chloride," filed in the U.S. Patent and Trademark Office May 16, 2018.
Le, Guillaume, et al., U.S. Appl. No. 15/982,625 entitled "Dissociation of a 1,4-Bis(4-Phenoxybenzoyl)Benzene—Lewis Acid Complex in an Aqueous Solution," filed in the U.S. Patent and Trademark Office May 17, 2018.
Jouanneau, Julien, et al., U.S. Appl. No. 15/982,453 entitled "Ripening of 1,4-Bis(4-Phenoxybenzoyl)Benzene," filed in the U.S. Patent and Trademark Office May 17, 2018.
Le, Guillaume, et al., U.S. Appl. No. 15/982,549 entitled "Purification of 1,4-Bis(4-Phenoxybenzoyl)Benzene by Centrifugal Filtration," filed in the U.S. Patent and Trademark Office May 17, 2018.
U.S. Appl. No. 16/186,039, filed Nov. 9, 2018, Julien Jouanneau, Guillaume Le, Steven Schon, John Richardson, Guillaume Vincent, Jérôme Amstutz (Cited herein as US Patent Application Publication No. 2019/0077739 A1 of Mar. 14, 2019).
International Search Report and Written Opinion, issued in PCT/EP2018/062803, dated Jul. 12, 2018, European Patent Office, Rijswijk, NL, 10 pages.
International Search Report and Written Opinion, issued in PCT/EP2018/062796, dated Aug. 20, 2018, European Patent Office, Rijswijk, NL, 7 pages.
International Search Report and Written Opinion, issued in PCT/EP2018/062813, dated Jun. 29, 2018, European Patent Office, Rijswijk, NL, 11 pages.
International Search Report and Written Opinion, issued in PCT/EP2018/063013, dated Jul. 24, 2018, European Patent Office, Rijswijk, NL, 8 pages.
International Search Report and Written Opinion, issued in PCT/EP2018/063017, dated Jul. 4, 2018, European Patent Office, Rijswijk, NL, 9 pages.
International Search Report and Written Opinion, issued in PCT/EP2018/063014, dated Jul. 24, 2018, European Patent Office, Rijswijk, NL, 10 pages.
Brown, R. R., et al., "Solubility and Activity of Aluminum Chloride in Aqueous Hydrochloric Acid Solutions," *RI 8379—Bureau of Mines Report of Investigations/1979*, 1979, United States Department of the Interior, Reproduced by National Technical Information Service, U.S. Department of Commerce, Springfield, VA 22161, 26 pages.
European Search Report in application No. EP 18306473.2, dated Apr. 18, 2019, European Patent Office, Munich, DE, 5 pages.
U.S. Appl. No. 16/609,648, Jouanneau et al.
U.S. Appl. No. 16/609,790, Le et al.
U.S. Appl. No. 16/613,587, Le et al.
U.S. Appl. No. 16/613,600, Jouanneau et al.
U.S. Appl. No. 16/613,454, Jouanneau et al.
U.S. Appl. No. 16/613,456, Le et al.
Jouanneau, Julien, et al., U.S. Appl. No. 16/609,648 entitled "Method for Manufacturing 1,4-Bis(4-Phenoxybenzoyl)Benzene at an Elevated Temperature," filed in the U.S. Patent and Trademark Office Oct. 30, 2019.
Le, Guillaume, et al., U.S. Appl. No. 16/609,790 entitled "Method for Manufacturing 1,4-Bis(4-Phenoxybenzoyl)Benzene in Supersaturation Conditions," filed in the U.S. Patent and Trademark Office Oct. 31, 2019.
Le, Guillaume, et al., U.S. Appl. No. 16/613,587 entitled "Method for Manufacturing 1,4-Bis(4-Phenoxybenzoyl)Benzene Using Substantially Non-Hydrolyzed Terephthaloyl Chloride," filed in the U.S. Patent and Trademark Office Nov. 14, 2019.
Jouanneau, Julien, et al., U.S. Appl. No. 16/613,600 entitled "Dissociation of a 1,4-Bis(4-Phenoxybenzoyl)Benzene-Lewis Acid Complex in an Aqueous Solution," filed in the U.S. Patent and Trademark Office Nov. 14, 2019.
Jouanneau, Julien, et al., U.S. Appl. No. 16/613,454 entitled "Ripening of 1,4-Bis(4-Phenoxybenzoyl)Benzene," filed in the U.S. Patent and Trademark Office Nov. 14, 2019.
Le, Guillaume, et al., U.S. Appl. No. 16/613,456 entitled "Purification of 1,4-Bis(4-Phenoxybenzoyl)Benzene by Centrifugal Filtration," filed in the U.S. Patent and Trademark Office Nov. 14, 2019.

METHOD FOR MANUFACTURING 1,4-BIS (4-PHENOXYBENZOYLBENZENE) AT AN ELEVATED TEMPERATURE

CROSS REFERENCE TO RELATED APPLICATIONS

The present application claims the benefit of European Application No. 17305559, filed on May 16, 2017. The entire contents of European Application No. 17305559, European Application No. 17305561, European Application No. 17305562, European Application No. 17305581, European Application No. 17305582, and European Application No. 17305583 are hereby incorporated herein by reference in their entirety.

TECHNICAL FIELD

The present application relates to a method for manufacturing 1,4-bis(4-phenoxybenzoyl)benzene, as well as polyether ketone ketone polymers starting from said 1,4-bis 4-phenoxybenzoyl)benzene.

TECHNICAL BACKGROUND

Polyether ketone ketone (PEKK) polymers have a number of properties which make them useful in applications involving exposure to high temperature or to high mechanical or chemical stress. They are, for instance, useful in the aerospace industry, in off-shore drilling and in medical devices.

One known route for manufacturing polyether ketone ketone polymers relies on the use of 1,4-bis(4-phenoxybenzoyl)benzene as a starting material.

1,4-bis(4-phenoxybenzoyl)benzene can be prepared by reacting terephthaloyl chloride and diphenyl ether in the presence of a Lewis acid, such as aluminum trichloride.

In document U. S. 4,816,556 (example 2), 1,4-bis 4-phenoxybenzoyl)benzene is prepared by dissolving terephthaloyl chloride and diphenyl ether in ortho-dichlorobenzene, cooling to 0-5° C. and adding aluminum chloride with temperature kept below 5° C. The mixture is then warmed to 20° C. Thereafter, cold methanol is added so as to produce a slurry which is filtered, reslurried in methanol and filtered again.

In document U. S. 4,826,947 (example 2), 1,4-bis(4-phenoxybenzoyl)benzene is prepared by providing a mixture of methylene chloride, methylsulfone and aluminum trichloride, cooling to a temperature of between −30 and −35° C., and then adding diphenyl ether and thereafter terephthaloyl chloride. The reaction mixture is then poured into cold methanol so as to make a slurry which is then filtered.

Document WO 95/23821 (example 11) discloses providing aluminum chloride in ortho-dichlorobenzene cooled in an ice bath, and then adding terephthaloyl chloride and diphenyl ether. Thereafter, the reaction mixture is allowed to warm up to room temperature, stirred, and poured into a methanol concentrated HCl solution. A precipitate is formed which is subsequently filtered off.

There is still a need for a method for manufacturing 1,4-bis(4-phenoxybenzoyl)benzene with a high purity and a high yield, which can be implemented at the industrial scale in an economically realistic manner.

SUMMARY

It is an object of embodiments of the invention to provide a method for manufacturing 1,4-bis(4-phenoxybenzoyl)benzene, comprising:

providing a reactant mixture comprising terephthaloyl chloride and diphenyl ether in a solvent;

adding a Lewis acid to the reactant mixture, so as to obtain a product mixture;

wherein the temperature of the reactant mixture is greater than 5° C. during at least part of the step of adding the Lewis acid to the reactant mixture.

In some embodiments, the Lewis acid is aluminum trichloride.

In some embodiments, the temperature of the reactant mixture is at least 15° C., preferably at least 25° C., or at least 35° C. or at least 45° C. during at least part of the step of adding the Lewis acid to the reactant mixture.

In some embodiments, the temperature of the reactant mixture is at least 30° C., preferably at least 40° C. and more preferably at least 45° C., after 20% by weight of Lewis acid has been added to the reactant mixture, relative to the total weight of Lewis acid added to the reactant mixture.

In some embodiments, the temperature of the reactant mixture increases during the step of adding the Lewis acid to the reactant mixture, from an initial temperature to a final temperature.

In some embodiments, the initial temperature is from −30° C. to 30° C., preferably from −15° C. to 25° C. and even more preferably from 0 to 20° C.

In some embodiments, the final temperature is at least 30° C., preferably at least 40° C., more preferably at least 45° C. and most preferably at least 50° C.

In some embodiments, the temperature of the reactant mixture does not exceed 100° C., preferably 90° C., more preferably 80° C., even more preferably 70° C., during the step of adding the Lewis acid.

In some embodiments, the solvent is a separate solvent and may be ortho-dichlorobenzene. In some embodiments, the solvent may be diphenyl ether.

In some embodiments, the method comprises the additional steps of:

mixing the product mixture with a protic solvent so as to provide a product slurry;

separating 1,4-bis(4-phenoxybenzoyl)benzene from the product slurry, preferably by filtration and optionally washing.

Another object of embodiments of the invention is a method of making a polyether ketone ketone polymer, comprising:

manufacturing 1,4-bis 4-phenoxybenzoyl)benzene according to the method described above;

reacting said 1,4-bis(4-phenoxybenzoyl)benzene with at least one difunctional aromatic acyl chloride.

Embodiments of the present invention provide a method for manufacturing 1,4-bis(4-phenoxybenzoyl)benzene with a high purity and a high yield. For example, the yield may be 85% or higher. This method can be implemented at the industrial scale.

In particular, by performing the reaction between terephthaloyl chloride and diphenyl ether in the presence of a Lewis acid at a higher temperature than in the prior art, it was surprisingly discovered that not only the yield of 14-bis 4-phenoxybenzoyl)benzene is increased, but also the level of by-product impurities, such as molecules containing xanthydrol moieties, remains low. Therefore, the method may be more efficient than in the prior art.

DETAILED DESCRIPTION OF EMBODIMENTS

Embodiments of the invention will now be described in more detail without limitation in the following description.

1,4-bis(4-phenoxybenzoyl)benzene is the compound of formula I:

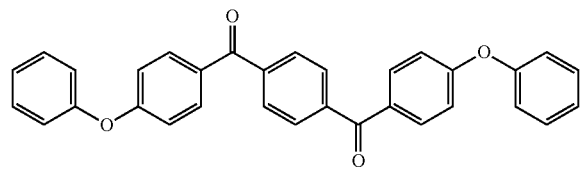

(I)

It may be made by reacting terephthaloyl chloride of formula II:

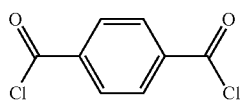

(II)

with diphenyl ether of formula III:

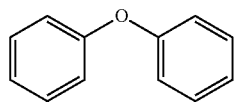

(III)

in a solvent, and in the presence of a Lewis acid, acting as a Friedel-Crafts catalyst. The solvent may be a non-protic solvent, which can, in particular, be selected from methylene chloride, carbon disulfide, ortho-dichlorobenzene, meta-dichlorobenzene, para-dichlorobenzene, 1,2,4-trichlorobenzene, 1,2,3-trichlorobenzene, ortho-difluorobenzene, 1,2-dichloroethane, 1,1,2,2-tetrachloroethane, tetrachloroethylene, dichloromethane, nitrobenzene and mixtures thereof.

Ortho-dichlorobenzene is a preferred solvent.

Lewis acids which may be used include, for example, aluminum trichloride, aluminum tribromide, antimony pentachloride, antimony pentafluoride, indium trichloride, gallium trichloride, boron trichloride, boron trifluoride, zinc chloride, ferric chloride, stannic chloride, titanium tetrachloride, and molybdenum pentachloride. Aluminum trichloride, boron trichloride, aluminum tribromide, titanium tetrachloride, antimony pentachloride, ferric chloride, gallium trichloride, and molybdenum pentachloride are preferred. Aluminum trichloride is preferred.

The reaction between the compounds of formulas II and III to make the compound of formula I may be performed in a glass reactor, a glass-lined reactor or a stainless-steel reactor.

According to some variations, the materials introduced into the reactor in a method of embodiments of the invention consist essentially, or consist, of the compounds of formulas II and III, the solvent and the Lewis acid.

According to embodiments of the invention, an initial reactant mixture comprising (or preferably consisting of) terephthaloyl chloride and diphenyl ether in a separate solvent is provided. The reactant mixture can be made by mixing the three components together, in any order. By way of example, the solvent can be introduced first into the reactor, and then the two reactants can be added to the reactor.

As a second step, the Lewis acid may be added to the reactant mixture. Preferably, the Lewis acid is added as a solid. Alternatively, the Lewis acid can also be added as a suspension or a solution, preferably in the abovementioned solvent.

In some variations, the Lewis acid is added in a particulate form, such as in the form of granules (having, e.g., a Dv80 of more than 1 mm) or in the form of a powder (having, e.g., a Dv80 of less than 1 mm, and preferably a Dv50 of less than 0.5 mm). Dv80 and Dv50 are respectively the particle sizes at the $80^{th}$ and $50^{th}$ percentiles (in volume) of the cumulative size distribution of the Lewis acid particles. These parameters may be determined by sieving.

In some particular embodiments, the weight concentrations and weight ratios of the reactants and of the catalyst are as follows:

the concentration of terephthaloyl chloride (relative to the sum of solvent, terephthaloyl chloride, diphenyl ether and Lewis acid introduced into the reactor) is from 2 to 25%, preferably from 3 to 12%, preferably from 5 to 10%;

the concentration of diphenyl ether (relative to the sum of solvent, terephthaloyl chloride, diphenyl ether and Lewis acid introduced into the reactor) is from 2 to 42%, preferably from 5 to 35%, preferably from 12 to 25%;

the concentration of Lewis acid (relative to the sum of solvent, terephthaloyl chloride, diphenyl ether and Lewis acid introduced into the reactor) is from 3 to 33%, preferably from 4 to 30%, preferably from 10 to 25%;

the weight ratio of terephthaloyl chloride to diphenyl ether introduced into the reactor is from 0.05 to 0.6, preferably from 0.2 to 0.6, preferably from 0.3 to 0.5;

the weight ratio of Lewis acid to terephthaloyl chloride plus diphenyl ether introduced into the reactor is from 0.2 to 0.9, preferably from 0.3 to 0.7.

The addition of the Lewis acid may be performed progressively, over a period of time which can advantageously range from 5 to 600 minutes, preferably from 30 to 300 minutes.

The addition can be performed continuously or with one or more interruptions. If it is performed continuously, it can be conducted at a constant rate of addition. Alternatively, the rate of addition can vary over time.

The reactant mixture may be agitated during at least part of the reaction. Thus, the reactor is preferably provided with an agitation device, such as a mechanical stirrer (which may, e.g., comprise one or more impellers) or a recirculation loop with a pump.

Preferably, the reactant mixture may be agitated using the agitation device during the addition of the Lewis acid.

The reaction at stake is exothermic. Preferably, a temperature control system is provided, in order to control the temperature of the reactant mixture in the reactor, in particular during and after addition of the Lewis acid. The temperature control system may in particular comprise a temperature sensor within the reactor and may be configured to cool and/or to heat the reactant mixture. Preferably, it is at least configured to cool the reactant mixture.

Devices for heating and/or cooling the reactant mixture may include a heat exchanger inside the reactor or in a recirculation loop, or a heat exchange fluid circuit in the jacket of the reactor.

When the temperature of the reactant mixture increases during the step of adding the Lewis acid, this can be achieved in three different manners:

by heating the reactant mixture (while preferably also controlling the rate of addition of the Lewis acid, so as to achieve a targeted increase in temperature);

by simply controlling the rate of addition of the Lewis acid so as to achieve a targeted increase in temperature, without providing external cooling or heating;

or by cooling the reactant mixture, while also controlling the rate of addition of the Lewis acid, so as to achieve a targeted increase in temperature.

According to a preferred embodiment, the reactant mixture is cooled during and possibly also after the step of adding the Lewis acid, in order to prevent an excessively large or rapid increase in temperature of the reactant mixture as the reactants start reacting with each other.

According to embodiments of the invention, the temperature of the reactant mixture is greater than 5° C. during at least part of the step of adding the Lewis acid to the reactant mixture. In particular variations of embodiments of the invention, the temperature of the reactant mixture is at least 10° C., or at least 15° C., or at least 20° C., or at least 25° C., or at least 30° C., or at least 35° C., or at least 40° C., or at least 45° C., or at least 50° C., or at least 55° C., or at least 60° C., during at least part of the step of adding the Lewis acid to the reactant mixture.

On the other hand, the temperature during the step of adding the Lewis acid to the reactant mixture should preferably remain below a certain threshold, for example, 120° C., in order to avoid any significant polymerization of the reactants into a PEKK polymer.

Furthermore, the temperature during the step of adding the Lewis acid to the reactant mixture should remain below the boiling temperature of the solvent.

It is possible to operate the reactor in a pressurized manner so that the temperature in the reactor can reach a higher value without causing the solvent to boil. In this case, the pressure in the reactor can range from 1 bar (atmospheric pressure) to 6 bar, preferably from 1.5 bar to 3 bar.

Alternatively, and preferably, the reaction is performed at atmospheric pressure.

According to some variants, the temperature of the reactant mixture does not exceed 100° C., preferably 90° C., more preferably 80° C., even more preferably 70° C., during the step of adding the Lewis acid.

It is believed that it may be more beneficial for the temperature of the reactant mixture to be relatively high at the end of the step of adding the Lewis acid than at the beginning of this step, in order to achieve some or all of the advantageous effects of embodiments of the invention. However, a temperature gradient is not required.

Accordingly, in some variants, once 90% by weight of Lewis acid has been added to the reactant mixture (relative to the total weight of Lewis acid added to the reactant mixture), it is preferred that the temperature of the reactant mixture is and remains of at least 5° C., preferably at least 10° C., or at least 15° C., or at least 20° C., or at least 25° C., or at least 30° C., or at least 35° C., or at least 40° C., or at least 45° C., or at least 50° C., or at least 55° C., or at least 60° C., during the remainder of the step of adding the Lewis acid to the reactant mixture.

In some variants, once 75% by weight of Lewis acid has been added to the reactant mixture (relative to the total weight of Lewis acid added to the reactant mixture), it is preferred that the temperature of the reactant mixture is and remains of at least 5° C., preferably at least 10° C., or at least 15° C., or at least 20° C., or at least 25° C., or at least 30° C., or at least 35° C., or at least 40° C., or at least 45° C., or at least 50° C., or at least 55° C., or at least 60° C., during the remainder of the step of adding the Lewis acid to the reactant mixture.

In some variants, once 50% by weight of Lewis acid has been added to the reactant mixture (relative to the total weight of Lewis acid added to the reactant mixture), it is preferred that the temperature of the reactant mixture is and remains of at least 5° C., preferably at least 10° C., or at least 15° C., or at least 20° C., or at least 25° C., or at least 30° C., or at least 35° C., or at least 40° C., or at least 45° C., or at least 50° C., or at least 55° C., or at least 60° C., during the remainder of the step of adding the Lewis acid to the reactant mixture.

In some variants, once 20% by weight of Lewis acid has been added to the reactant mixture (relative to the total weight of Lewis acid added to the reactant mixture), it is preferred that the temperature of the reactant mixture is and remains of at least 5° C., preferably at least 10° C., or at least 15° C., or at least 20° C., or at least 25° C., or at least 30° C., or at least 35° C., or at least 40° C., or at least 45° C., or at least 50° C., or at least 55° C., or at least 60° C., during the remainder of the step of adding the Lewis acid to the reactant mixture.

The temperature of the reactant mixture can remain constant during the step of adding the Lewis acid. Alternatively, it can vary during this step.

By "initial temperature" is meant the temperature of the reactant mixture at the beginning of the step of adding the Lewis acid, i.e., as the first molecules of Lewis acid are added to the reactant mixture.

By "final temperature" is meant the temperature of the reactant mixture at the end of the step of adding the Lewis acid, i.e., as the last molecules of Lewis acid are added to the reactant mixture.

The initial temperature of the reactant mixture may range from, e.g., −30° C. to 80° C.

In some variations, the initial temperature of the reactant mixture is from −30 to −25° C.; or from −25 to −20° C.; or from −20 to −15° C.; or from −15 to −10° C.; or from −10 to −5° C.; or from −5 to −0° C.; or from 0 to 5° C.; or from 5 to 10° C.; or from 10 to 15° C.; or from 15 to 20° C.; or from 20 to 25° C.; or from 25 to 30° C.; or from 30 to 35° C.; or from 35 to 40° C.; or from 40 to 45° C.; or from 45 to 50° C.; or from 50 to 55° C.; or from 55 to 60° C.; or from 60 to 65° C.; or from 65 to 70° C.; or from 70 to 75° C.; or from 75 to 80° C. Ranges of from 0 to 80° C., more particularly from 20 to 50° C. are preferred.

The final temperature of the reactant mixture may range from, e.g., 10° C. to 80° C. In some variations, the final temperature of the reactant mixture is from 10 to 15° C.; or from 15 to 20° C.; or from 20 to 25° C.; or from 25 to 30° C.; or from 30 to 35° C.; or from 35 to 40° C.; or from 40 to 45° C.; or from 45 to 50° C.; or from 50 to 55° C.; or from 55 to 60° C.; or from 60 to 65° C.; or from 65 to 70° C.; or from 70 to 75° C.; or from 75 to 80° C. Ranges of from 30 to 80° C., and more particularly from 40 to 70° C., even more particularly from 45 to 60° C. are preferred. In some variations, the final temperature is at least 30° C., preferably at least 40° C., more preferably at least 45° C. and most preferably at least 50° C.

In some variations, the temperature of the reactant mixture decreases during the step of adding the Lewis acid, i.e. the final temperature is lower than the initial temperature.

In preferred variations, the temperature of the reactant mixture increases during the step of adding the Lewis acid, i.e., the final temperature is greater than the initial temperature.

In some embodiments, the temperature difference ΔT between the final temperature and the initial temperature is from 1 to 120° C., preferably from 1 to 70° C., preferably from 5 to 60° C., more preferably from 10 to 50° C., and in particular from 20 to 40° C.

In some variations, the increase in temperature is monotonous, i.e. there is no transient decrease in temperature during the entire step of adding the Lewis acid. On the other hand, transient variations or fluctuations in temperature are possible in some embodiments, especially due to the non-instantaneous nature of the temperature control.

In some variations, the temperature of the reactant mixture continuously increases from the initial temperature to the final temperature. Alternatively, the temperature of the reactant mixture may comprise one or more increase stages and one more plateau stages during the step of adding the Lewis acid. In particular, the temperature of the reactant mixture may initially increase during a first part of the step of adding the Lewis acid, from the initial temperature to the final temperature, and then plateau at the final temperature during a second part of the step of adding the Lewis acid. In this case, the plateau temperature may be set with a precision of, e.g., +/−5° C., or +/−2° C., or +/−1° C.

Once the step of adding the Lewis acid to the reactant mixture is complete, the reactant mixture can optionally be maintained, preferably under agitation, for a certain time, in order to complete the reaction to the desired degree. Preferably, the mixture is maintained from 0 to 600 min, more preferably from 5 to 180 min.

There is no limitation as to the temperature of the reactant mixture during this step of maintaining the reactant mixture. In some variations, the temperature of the mixture is maintained at the final temperature described above. In other variations, it increases or decreases relative to the final temperature.

Once the reaction is completed to the desired degree, the reactant mixture becomes designated as a product mixture.

The method of embodiments of the invention advantageously comprises one or more steps for purifying 1,4-bis(4-phenoxybenzoyl)benzene from the product mixture, and in particular from the solvent, catalyst and unreacted reactants as well as by-products. The purification may comprise the steps of:
  mixing the product mixture with a protic solvent so as to provide a product slurry;
  separating 1,4-bis(4-phenoxybenzoyl)benzene from the product slurry, preferably by filtration and washing.

The protic solvent used to make the product slurry is advantageously selected so that 1,4-bis(4-phenoxybenzoyl)benzene tends to precipitate. By way of example, methanol may be used as a protic solvent.

The protic solvent can be an organic solvent, such as methanol, acetic acid, formic acid, ethanol, isopropanol, and benzyl alcohol.

Alternatively, the protic solvent can be an aqueous solution.

Mixtures of the above solvents can also be used, such as an aqueous-organic solvent, e.g., an aqueous solution mixed with methanol.

The desired product can then be recovered from the product slurry by filtration. If necessary, the product can be washed, preferably by a protic solvent such as methanol, and filtrated again, once or several times. Washing can be performed for example by re-slurrying the product in the solvent.

The 1,4-bis(4-phenoxybenzoyl)benzene obtained according to embodiments of the invention can subsequently be used to perform a polymerization reaction so as to make a PEKK polymer.

In order to make the PEKK polymer, 1,4-bis 4-phenoxybenzoyl)benzene is reacted with at least one difunctional aromatic acyl chloride.

The difunctional aromatic acyl chloride may in particular include terephthaloyl chloride, isophthaloyl chloride and more preferably a mixture of terephthaloyl chloride and isophthaloyl chloride.

The reaction is preferably implemented in a solvent. The solvent is preferably a non-protic solvent, which can in particular be selected from methylene chloride, carbon disulfide, ortho-dichlorobenzene, meta-dichlorobenzene, para-dichlorobenzene, 1,2,4-trichlorobenzene, ortho-difluorobenzene, 1,2-dichloroethane, 1,1,2,2-tetrachloroethane, tetrachloroethylene, dichloromethane, nitrobenzene and mixtures thereof.

The reaction is preferably implemented in the presence of a Lewis acid as a catalyst.

Lewis acids which may be used include, for example, aluminum trichloride, aluminum tribromide, antimony pentachloride, antimony pentafluoride, indium trichloride, gallium trichloride, boron trichloride, boron trifluoride, zinc chloride, ferric chloride, stannic chloride, titanium tetrachloride, and molybdenum pentachloride. Aluminum trichloride, boron trichloride, aluminum tribromide, titanium tetrachloride, antimony pentachloride, ferric chloride, gallium trichloride, and molybdenum pentachloride are preferred. Aluminum trichloride is particularly preferred.

The polymerization can be implemented in the same reactor as the one used for the production of 1,4-bis(4-phenoxybenzoyl)benzene. But more preferably it is implemented in one or more other reactors.

The polymerization can be carried out at a temperature ranging from, e.g., 50 to 120° C.

The method of making the PEKK polymer advantageously also comprises one or more steps for purifying the PEKK polymer, such as steps of:
  mixing the mixture containing the PEKK polymer with a protic solvent so as to provide a PEKK slurry;
  separating the PEKK polymer from the PEKK slurry, preferably by filtration and washing.

The protic solvent used to make the PEKK slurry may be, e.g., methanol.

The PEKK polymer can then be recovered from the PEKK slurry by filtration. If necessary, the polymer can be washed, preferably by a protic solvent such as methanol, and filtrated again, once or several times. Washing can be performed for example by re-slurrying the polymer in the solvent.

EXAMPLES

The following examples illustrate embodiments of the invention without limiting the invention.

Example 1 (Comparative)

In a 2 L reactor equipped with a mechanical stirrer, with a nitrogen inlet and outlet going to a scrubber system, 1470 g of ortho-dichlorobenzene, 92.7 g of terephthaloyl chloride and 233 g of diphenyloxide were introduced.

After full solubilization, the mixture was cooled to 0° C. While keeping the temperature at 0° C., 198 g of AlCl$_3$ were slowly added to the reactant mixture. After completion of AlCl₃ addition, the mixture was kept agitated at 0° C. during 3 hours to finish the reaction. Then a sample was taken, quenched in methanol and analyzed with 1H NMR. The relative molar composition of the desired product, by-products and unconverted terephthaloyl chloride (in the esterified form of dimethyl terephthalate) was calculated based on the characteristic peaks of the relevant species.

Examples 2-4 (According to Embodiments of the Invention)

Experiments analogous to example 1 were performed but with a reaction carried out at 25° C. (example 2), at 40° C. (example 3) or at a temperature increasing from a starting temperature of 24° C. to a final temperature of 30° C. reached after 68% of the AlCl₃ addition (example 4).

The following table summarizes the results obtained in examples 1-4. The yield in 1,4-bis(4-phenoxybenzoyl)benzene is indicated in the fourth line. The molar fraction of molecules containing xanthydrol moieties and 4-phenoxy benzoyl benzoic methyl-ester impurities are indicated in the last two lines.

| Example No. | 1 | 2 | 3 | 4 |
|---|---|---|---|---|
| Synthesis temperature | 0° C. | 25° C. | 40° C. | 24 to 30° C. |
| Mol % dimethyl terephthalate | 0 | 0 | 0 | 0 |
| Mol % 1,4-bis (4-phenoxybenzoylbenzene) | 80 | 85 | 90 | 87 |
| Mol % xanthydrol moiety-containing molecules | 4 | 4 | 4 | 3 |
| Mol % 4-(4-phenoxy benzoyl) benzoic acid methyl-ester | 16 | 11 | 6 | 9 |

EMBODIMENTS

1. A method for manufacturing 1,4-bis 4-phenoxybenzoyl) benzene, comprising:
   providing a reactant mixture comprising terephthaloyl chloride and diphenyl ether in a solvent;
   adding a Lewis acid to the reactant mixture, so as to obtain a product mixture;
   wherein the temperature of the reactant mixture is greater than 5° C. during at least part of the step of adding the Lewis acid to the reactant mixture.
2. The method of embodiment 1, wherein the Lewis acid is aluminum trichloride.
3. The method of embodiment 1 or 2, wherein the temperature of the reactant mixture is at least 15° C., preferably at least 25° C., or at least 35° C. or at least 45° C. during at least part of the step of adding the Lewis acid to the reactant mixture.
4. The method of any one of embodiments 1 to 3, wherein the temperature of the reactant mixture is at least 30° C., preferably at least 40° C. and more preferably at least 45° C., after 20% by weight of Lewis acid has been added to the reactant mixture, relative to the total weight of Lewis acid added to the reactant mixture.
5. The method of any one of embodiments 1 to 4, wherein the temperature of the reactant mixture increases during the step of adding the Lewis acid to the reactant mixture, from an initial temperature to a final temperature.
6. The method of embodiment 5, wherein the initial temperature is from 0 to 80° C., preferably from 30° C. to 50° C.
7. The method of embodiment 5 or 6, wherein the final temperature is at least 30° C., preferably at least 40° C., more preferably at least 45° C. and most preferably at least 50° C.
8. The method of any one of embodiments 1 to 7, wherein the temperature of the reactant mixture does not exceed 100° C., preferably 90° C., more preferably 80° C., even more preferably 70° C., during the step of adding the Lewis acid.
9. The method of any one of embodiments 1 to 8, wherein the solvent is ortho-dichlorobenzene.
10. The method of any one of embodiments 1 to 9, wherein a temperature difference between a final temperature and an initial temperature is from 1 to 120° C., preferably from 1 to 70° C., preferably from 5 to 60° C., more preferably from 10 to 50° C., and in particular from 20 to 40° C.
11. The method of any of embodiments 1-10, wherein the solvent is a separate solvent from the diphenyl ether.
12. The method of any of embodiments 1-11, wherein the concentration of terephthaloyl chloride (relative to a sum of the solvent, the terephthaloyl chloride, the diphenyl ether and the Lewis acid) is from 2 to 25%, preferably from 3 to 12%, preferably from 5 to 10%.
13. The method of any of embodiments 1-12, wherein the concentration of diphenyl ether (relative to a sum of the solvent, the terephthaloyl chloride, the diphenyl ether and the Lewis acid) is from 2 to 42%, preferably from 5 to 35%, preferably from 12 to 25%.
14. The method of any of embodiments 1-13, wherein the weight ratio of terephthaloyl chloride to diphenyl ether introduced into the reactor is from 0.05 to 0.6, preferably from 0.2 to 0.6, preferably from 0.3 to 0.5.
15. The method of any one of embodiments 1 to 14, comprising additional steps of:
   mixing the product mixture with a protic solvent so as to provide a product slurry;
   separating 1,4-bis(4-phenoxybenzoyl)benzene from the product slurry, preferably by filtration and optionally washing.
16. A method of making a polyether ketone ketone polymer, comprising:
   manufacturing 1,4-bis (4-phenoxybenzoyl)benzene according to the method of any one of embodiments 1 to 15;
   reacting said 1,4-bis(4-phenoxybenzoyl)benzene with at least one difunctional aromatic acyl chloride.

The invention claimed is:
1. A method for manufacturing 1,4-bis(4-phenoxybenzoyl)benzene, comprising:
   providing a reactant mixture comprising terephthaloyl chloride and diphenyl ether in a solvent; and
   adding a Lewis acid to the reactant mixture, so as to obtain a product mixture;
   wherein the temperature of the reactant mixture is greater than 5° C. during at least part of the step of adding the Lewis acid to the reactant mixture.
2. The method of claim 1, wherein the Lewis acid is aluminum trichloride.
3. The method of claim 1, wherein the temperature of the reactant mixture is at least 15° C. during at least part of the step of adding the Lewis acid to the reactant mixture.
4. The method of claim 1, wherein the temperature of the reactant mixture is at least 30° C. after 20% by weight of Lewis acid that has been added to the reactant mixture, relative to the total weight of Lewis acid added to the reactant mixture.
5. The method of claim 1 wherein the temperature of the reactant mixture increases during the step of adding the Lewis acid to the reactant mixture, from an initial temperature to a final temperature.

6. The method of claim 5, wherein the initial temperature is from 0 to 80° C.

7. The method of claim 5, wherein the final temperature is at least 30° C.

8. The method of claim 1, wherein the temperature of the reactant mixture does not exceed 100° C. during the step of adding the Lewis acid.

9. The method of claim 1, wherein the solvent is ortho-dichlorobenzene.

10. The method of claim 1, wherein a temperature difference between a final temperature and an initial temperature is from 1 to 120° C.

11. The method of claim 1, wherein the solvent is a separate solvent from the diphenyl ether.

12. The method of claim 1, wherein the concentration of terephthaloyl chloride relative to a sum of the solvent, the terephthaloyl chloride, the diphenyl ether and the Lewis acid is from 2 to 25%.

13. The method of claim 1, wherein the concentration of diphenyl ether relative to a sum of the solvent, the terephthaloyl chloride, the diphenyl ether and the Lewis acid is from 2 to 42%.

14. The method of claim 1, wherein the weight ratio of terephthaloyl chloride to diphenyl ether introduced into the reactor is from 0.05 to 0.6.

15. The method of claim 1, further comprising steps of:
mixing the product mixture with a protic solvent so as to provide a product slurry; and
separating 1,4-bis(4-phenoxybenzoyl)benzene from the product slurry and optionally washing.

16. A method of making a polyether ketone ketone polymer, comprising:
manufacturing 1,4-bis(4-phenoxybenzoyl)benzene according to the method of claim 1; and
reacting said 1,4-bis(4-phenoxybenzoyl)benzene with at least one difunctional aromatic acyl chloride.

17. A method for manufacturing 1,4-bis(4-phenoxybenzoyl)benzene, comprising:
providing terephthaloyl chloride, diphenyl ether, a solvent and a Lewis acid;
reacting the terephthaloyl chloride with the diphenyl ether in the solvent, and in the presence of the Lewis acid, so as to obtain a product mixture, wherein the temperature of the reacting mixture is greater than 5° C. during at least part of the duration of the reaction; and
recovering the product mixture comprising a 1,4-bis(4-phenoxybenzoyl)benzene-Lewis acid complex.

* * * * *